(12) United States Patent
Hollering et al.

(10) Patent No.: US 6,274,085 B1
(45) Date of Patent: *Aug. 14, 2001

(54) DEVICE FOR INVESTIGATING NON-LINEAR OPTICAL BEHAVIOR OF A LAYER FORMED FROM FIRST AND SECOND REACTANTS

(75) Inventors: Robertus W. J. Hollering; Maarten Barmentlo, both of Eindhoven (NL)

(73) Assignee: U.S. Philips Corporation, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/393,943

(22) Filed: Sep. 10, 1999

Related U.S. Application Data

(63) Continuation of application No. 08/809,437, filed as application No. PCT/IB96/00806 on Aug. 16, 1996, now Pat. No. 5,976,891.

(30) Foreign Application Priority Data

Aug. 22, 1995 (EP) .................................................. 95202254

(51) Int. Cl.[7] .................................................. G01N 21/64
(52) U.S. Cl. ...................................... 422/82.05; 422/82.08
(58) Field of Search .............................. 422/82.05, 82.08; 436/524–527, 164, 172, 805

(56) References Cited

U.S. PATENT DOCUMENTS

| | | | |
|---|---|---|---|
| 4,446,239 | * 5/1984 | Tsuji et al. | 436/532 |
| 4,621,063 | * 11/1986 | Wyatt et al. | 436/501 |
| 4,820,649 | 4/1989 | Kawaguchi et al. | 436/501 |
| 5,123,731 | 6/1992 | Yoshinaga et al. | 356/73 |
| 5,156,810 | 10/1992 | Ribi | 422/82.01 |
| 5,179,005 | * 1/1993 | Phillips et al. | 435/14 |
| 5,437,840 | * 8/1995 | King et al. | 422/82.08 |
| 5,514,596 | 5/1996 | King et al. | 436/164 |

FOREIGN PATENT DOCUMENTS

| | | |
|---|---|---|
| 0395300A2 | 10/1990 | (EP) . |
| WO9104483 | 4/1991 | (WO) . |
| WO9403774 | 2/1994 | (WO) . |

OTHER PUBLICATIONS

Applied Optics, "Visual Detection of Organic Monomoleculary Films by Interference Colors", Torbjorn Sandstrom, Manne Stenberg, and Haken Nygren, Applied Optics/vol. 24, No. 4, Feb. 15, 1985, p. 472, See the Whole Document.
Dialog Information Services, File 2, Inspec, Dialog Accession No. 5056401, Inspec Abstract No. A9520–8780B–006, Verbiest, T. et al: 1994 IEEE Nonlinear Optics: Materials, Fundamentals, and Applications, Jul. 25–29, 1994, IEEE Catalog # 94CH3370–4, p. 80–2.
"Optical Second Harmonic Generation as a Probe of Surface Chemistry", Chem. Rev. 1994, vol. 94, Robert M. Corn and Daniel A. Higgins, pp. 107–125, See the Whole Document.

* cited by examiner

*Primary Examiner*—Jeffrey Snay
(74) *Attorney, Agent, or Firm*—John F. Vodopia

(57) ABSTRACT

A method and a device for optically ascertaining the mutual binding of a first and a second reactant are described. Use is made of the fact that a dipolar layer (7) having a non-linear optical behavior is formed upon a reaction between the two reactants. The formation of such a layer is ascertained by illuminating the substance with radiation (8) having one or two frequencies, and by detecting whether radiation (10) from the substance contains a component at a frequency which is twice the frequency, or a mixed term of the frequency of the radiation incident on the substance.

6 Claims, 2 Drawing Sheets

DEVICE FOR INVESTIGATING NON-LINEAR OPTICAL BEHAVIOR OF A LAYER FORMED FROM FIRST AND SECOND REACTANTS

CROSS REFERENCE TO RELATED APPLICATIONS

This is a continuation of application Ser. No. 08/809,437, filed Aug. 25, 1997, now U.S. Pat. No. 5,976,891, which was a National Stage of International Application Ser. No. PCT/IB96/00806, filed Aug. 16, 1996.

BACKGROUND OF THE INVENTION

1. Field of the Invention

The invention relates to a method of ascertaining the mutual binding of a first reactant and a second reactant, which method comprises the following steps:

providing a substance comprising the first reactant in a holder so that the substance is adsorbed at the inner side of the holder, adding a solution containing the second reactant to the holder, and irradiating the holder with electromagnetic radiation and detecting whether a parameter of radiation from the holder has changed with respect to said parameter of the radiation incident on the holder.

The invention also relates to a device for performing this method. In known methods, the radiation parameter which may change is, for example, the color or the state of polarization.

2. Description of the Related Art

The method is often used as an antibody virus detection in medical diagnostics for detecting infectious diseases at an early stage, with the virus being the first reactant and the antibody being the second reactant. An antibody, or possibly several antibodies in succession, are added to a substance containing an unknown virus so as to detect this virus. Moreover, for example, for developing medicines, a material which may be a possible antibody for the virus may be added to a known virus so as to ascertain whether this antibody reacts with the virus. The biological substance which is examined by means of the method may be human or animal tissue, blood or secretion.

Due to the considerable risks which may be involved in viral infections, which may occur, for example during pregnancy or birth, virus-antibody tests are nowadays performed in large numbers.

Therefore, there is a need for inexpensive and rapid virus detection methods, all the more because after a test with a first antibody and after it has been found that the virus does not react to this antibody, a second test and possibly subsequent tests, each time with a different antibody, must be performed.

For detecting the presence of a virus, the method described in the opening paragraph is generally used in which, after addition to the substance of the solution with antibody to which Rhodamine 6G molecules are bound, an incubation time is observed in which the virus can react with the antibody.

Subsequently, the holder with the substance and the antibody is washed several times, for example four times, so that all antibodies which have not reacted with the substance are removed. Subsequently, it is ascertained by means of irradiation with light, whether there are still fluorescent Rhodamine 6G molecules present, hence whether there is still antibody. This antibody is then bound to the substance, in other words, it has reacted with a virus. If no fluorescence is observed, the substance does not contain a virus matching the antibody.

A great drawback of this method is that the washing operation must be performed frequently, which is time consuming and involves a waste of antibodies so that the method cannot be performed in situ. Moreover, the detection method is not very reliable.

To be able to detect in situ and to avoid the washing steps, alternative methods have been proposed which are based on optical techniques such as the detection of the quantity of light reflected by the substance, or of the change of the state of polarization of the light coming from the substance (ellipsometry) or of a technique known as the Fourier-transformed infrared (FTIR) technique.

PCT Patent Application No. 94/03774 describes a number of these techniques for detecting, inter alia, viruses which to this end are contacted with a thin layer in which antibodies are present and, if they react with an antibody, cause a change of an optical property such as the reflection coefficient, the polarization selectivity or the color selectivity.

For a reliable virus detection, only radiation from the surface of the antibody which is in contact with the substance to be examined should be detected. However, in the above-mentioned in situ detection methods, radiation from the holder may reach the detector, which radiation does not originate from this surface, hence of Rhodamine 6G molecules which are bound to antibody which has not reacted with the virus. Since no distinction can be made between Rhodamine 6G molecules which are bound to an antibody which has reacted with a virus and molecules which are bound to antibody but has not reacted with a virus, said in situ methods are not very reliable either.

SUMMARY OF THE INVENTION

It is an object of the present invention to provide a method of ascertaining the mutual binding of a first and a second reactant for providing, inter alia, virus detection which is simple, inexpensive and reliable. This method is characterized in that it is detected whether a layer having a non-linear optical behavior is formed at the interface between the first reactant and the second reactant.

This method provides the possibility of direct detection in situ, inter alia, whether a virus has reacted with an antibody. Then, a polar ordered molecular layer is produced at the interface between the substance and the antibody, which layer exhibits a non-linear optical behavior. As a result, a radiation component having a frequency which essentially differs from that of the radiation with which the surface of the holder is irradiated is produced when irradiating the holder surface on which the substance to be examined has deposited. If the substance does not contain any virus which reacts with the antibody, there is no formation of a polar ordered layer and no wavelength change. Due to the selective detection of radiation at a given frequency which has a given relation with that of the radiation with which the holder is irradiated, it is only ascertained that the dipolar layer has been formed or not formed, while possible radiation coming from antibody parts which have not reacted with a virus does not influence the detection. Consequently, the detection method according to the invention is very reliable.

There are different possibilities of ascertaining the formation of said dipolar layer.

A first principal embodiment of the method according to the invention is further characterized in that an incubation period is observed after the solution has been introduced into the holder, in which period the reactants can react with each other, whereafter it is ascertained whether said dipolar layer has been formed.

A second principal embodiment of the method according to the invention is alternatively characterized in that the detection is started immediately after the solution has been introduced into the holder, and in that it is ascertained whether and at which rate said dipolar layer is formed.

In the latter embodiment, use is made of the fact that also the rate at which a reaction between an antibody and a virus takes place, hence the rate at which a dipolar layer is formed, is characteristic of the kind of virus or of the kind of antibody, so that this kind can be determined by measuring the increase as a function of time of the radiation intensity incident on the detector.

The two principal embodiments may be further characterized in that the holder is irradiated with monochromatic radiation having a first frequency, and in that it is detected whether radiation from the substance has a frequency which is twice the first frequency. Use is then made of the second harmonic effect of the non-linear dipolar layer; that is, this layer doubles the frequency of radiation incident thereon and converts, for example, red light into blue light.

Alternatively, the two principal embodiments may be further characterized in that the holder is irradiated with two radiation components having a first and a second frequency, respectively, and in that it is detected whether radiation from the substrate has a frequency which is a mixed term of the first and the second frequency.

The mixed term may be the sum of the first and the second frequency, but also the difference between these frequencies.

To promote the formation of the dipolar layer and hence enhance the frequency conversion, the method according to the invention may be further characterized in that use is made of a reactant which is labeled with molecules which can be satisfactorily polarized non-linearly.

This material is, for example the dye Rhodamine 6G. Instead of Rhodamine 6G molecules, molecules of, for example Hemicyanine or Coumarine may alternatively be bound to the solution. Generally, dyes used in dye lasers may be used for this purpose.

It is to be noted that said PCT Patent Application No. 94/03774 describes methods in which use is made of a color change in the radiation coming from the substance to be examined. However, this color change is understood to mean that the radiation coming from the substance has a different combination of wavelengths or a different intensity distribution of the different wavelengths than the radiation incident on the substance. No use is made of a doubling of a single frequency or of sum and difference frequency generation.

The embodiment of the method according to the invention, in which frequency doubling is used, may be further characterized in that the presence of radiation having half a wavelength is ascertained visually. Use is made of the fact that the color change occurring upon generating the second harmonic is so large that it can easily be ascertained by the human eye. Then it is sufficient to use a simple device consisting of a monochromatic radiation source and a support for the substance holder.

In accordance with a further aspect of the invention, a novel device is used for performing the method, which device comprises:

a radiation source for supplying a radiation beam having at least one discrete frequency, a support for a holder to accommodate a first and a second reactant, a detection system for detecting radiation from the holder, which device is characterized in that the detection system is adapted to detect only radiation having a frequency which differs essentially from said at least one discrete frequency.

A detection which is more sensitive than the visual detection is possible when using this opto-electronic device. When using a laser as a radiation source, the detection by means of the device is safer than the visual detection.

To enhance the sensitivity of the detection device, it may be further characterized in that a lens system is arranged between the support and the radiation-sensitive detection system. A larger part of radiation coming from the substance can be focused on the detection system by means of such a lens system.

To ensure that the detection system reacts only to radiation having a changed frequency, the device may be further characterized in that this system comprises successively a filter which passes only radiation of the changed frequency, and a radiation-sensitive element which converts this radiation into an electric signal.

Alternatively, the detection device may be characterized in that the detection system comprises a radiation-sensitive element which converts radiation into an electric signal, and is preceded by a luminescent element which converts the radiation having the changed frequency and coming from the substrate into radiation having a frequency to which said radiation-sensitive element is sensitive.

The detection device may have a compact design if it is further characterized in that the radiation source is constituted by a diode laser.

The detection device is further preferably characterized in that the radiation-sensitive element is constituted by a photodiode.

The use of a photodiode enhances the possibility of giving the device a compact design.

A practical embodiment of the detection device is characterized in that the radiation source and the detection system are arranged in one housing having a wall facing the radiation source and the detection system, while at least a part of said wall is transparent to radiation having said wavelengths, which wall serves as a support for the holder.

These and other aspects of the invention will be apparent from and elucidated with reference to the embodiments described hereinafter.

In the drawings:

DETAILED DESCRIPTION OF THE PREFERRED EMBODIMENT

Figure 1A:
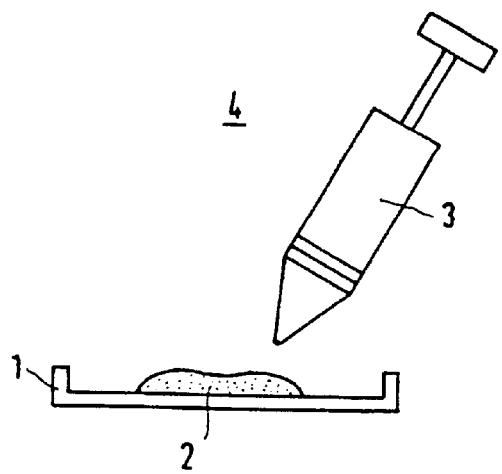
FIGS. 1a, 1b and 1c illustrate diagrammatically the method according to the invention.
Figure 1B:
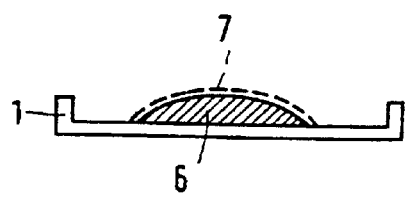
Figure 1C:
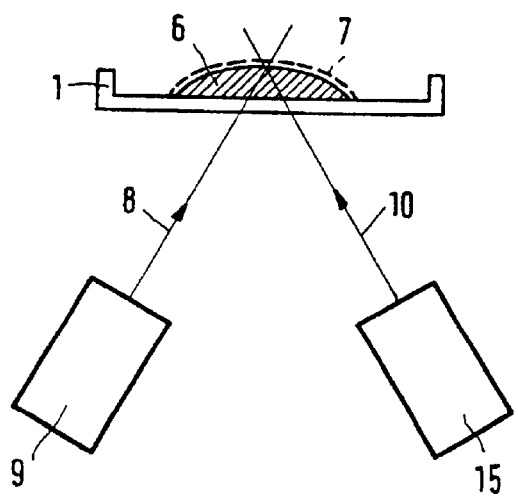

As is shown in FIG. 1a, a, for example biological substance 2 containing an unknown virus whose identity is to be ascertained, or containing a known virus by means of which possible antibodies are to be examined, is provided on a cover glass or in a shallow holder 1. This substance adheres to the inner wall of the holder or on the surface of the cover glass. An antibody 3 is added to this substance from a drop glass or tube 4 or by means of a Q-tip or spatula. Subsequently, the antibody is given the opportunity for a shorter or longer time, the incubation period, to react with the virus in the biological substrate, 6 in FIG. 1b. As is shown in FIG. 1c, the substance 6 is thereafter provided in the path of a radiation beam 8 originating from a radiation source which supplies, for example, monochromatic radiation at a first frequency, for example in the red or infrared wavelength range. The radiation 10 reflected by the substance is received by a detection system 15 which converts only radiation having a frequency of twice that of the radiation beam 8 into an electric signal Se. This signal can be converted into a visual indication, for example by causing a lamp to light up, or into an audio indication, for example a buzzer or ringing signal, or into another indication, for example the deflection of a pointer.

This method is based on the recognition, which has hitherto not been used in medical diagnostics and in immunology tests, that upon reaction of a virus with an antibody, its molecules form a dipolar layer 7. This layer has a non-linear optical behavior which becomes manifest in the generation of radiation at a frequency which differs essentially from the frequency of the radiation source. If radiation having a first frequency is incident on this layer, it is partly converted into radiation having a second frequency which is twice the first frequency. For example, upon a radiation with red light, this layer will bring about blue light.

The formation of said dipolar layer may also be detected by radiation with two components having a first frequency $\Omega_1$ and a second frequency $\Omega_2$, respectively. The dipolar layer converts a part of the radiation having these components into radiation having a third frequency $\Omega_3$ which is equal to the difference between the first and the second frequency, and into radiation having a fourth frequency $\Omega_4$ which is the sum of the first and the second frequency. Whether use is made of the double frequency or of the third or fourth frequency during detection depends on the availability of radiation sources and detectors. In current practice, a good combination for detection of the double frequency is a combination of an optical communication diode laser with a wavelength of 1300 nm or 1500 nm and a photomultiplier tube or a photodiode which are specially sensitive in the visible range. It is to be noted that frequency doubling by a layer having a non-linear optical effect is a special case of generating a difference frequency. If there is no reaction between an antibody and a virus, no linear optical layer is formed and there is no frequency doubling or frequency summing or subtraction.

The novel method is surface-selective, that is to say, only the phenomena occurring at the interface between the reactants, such as an antibody and the substance with the virus, are detected, and is insensitive to phenomena which occur in the holder space outside the substance. Moreover, the novel method may be performed rapidly, in situ and with a small number of ancillary means.

Instead of detection in reflection, as shown in FIG. 1c, it is also possible to detect in transmission. The radiation source is then arranged at one side of the substance and the detector is arranged at the opposite side. The advantage of detection in reflection is that the radiation to be detected passes a smooth surface, i.e. the surface of the holder or cover glass, twice, so that there is a small risk of dispersion.

To enhance the detection sensitivity, use is made of a second reactant, such as an antibody, to which, for example Rhodamine 6G molecules are bound. Upon reaction of the antibody with the virus, these molecules will also form part of the intermediate layer. Since they can be satisfactorily polarized non-linearly, they enhance the extent of non-linearity of this layer so that the frequency-doubling or frequency-mixing effect, and hence the detector signal, is increased. Instead of Rhodamine 6G, other substances exhibiting the same effect and known as dyes may be used. Specially suitable for this purpose are the dyes used in dye lasers such as Hemicyanine or Coumarine.

Figure 2:
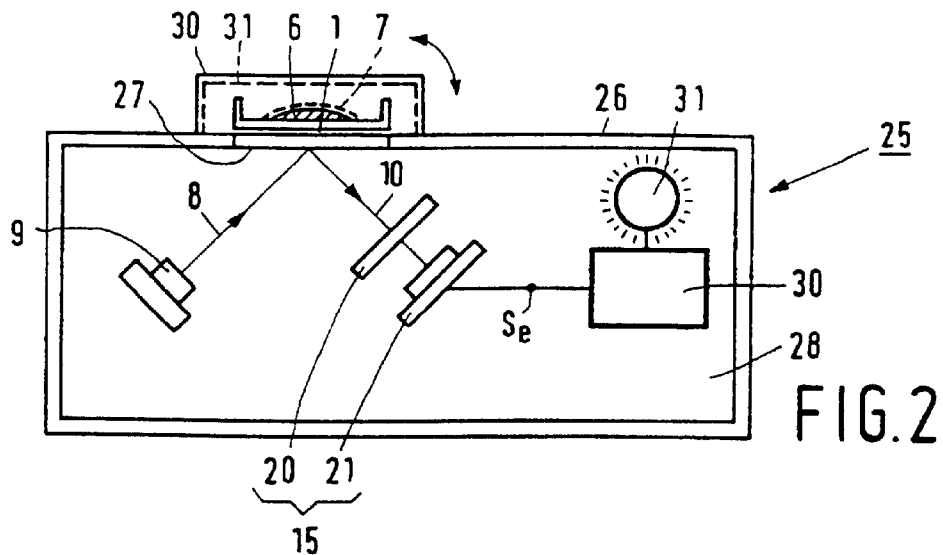
FIG. 2 shows a first embodiment of the device.

The device for performing the novel method has a simple structure, as in FIG. 2, showing a first embodiment of such a device. In this Figure, the reference numeral 9 denotes a radiation source, preferably in the form of a diode laser transmitting a beam of monochromatic radiation having a wavelength of, for example, 860 nm to a transparent holder 1 which contains the substance to be examined. The detection system 15 for converting the radiation reflected by the substance into an electric signal consists of an optical filter 20 which passes, for example radiation having a wavelength of 430 nm, and a photodiode 21. The diode laser 9 and the detection system 15 are arranged in a housing 25 having an upper face 26 a part 27 of which is transparent to radiation having a wavelength of 860 nm and to radiation having a wavelength of 430 nm. The rest of the upper face, the lower face and the side faces of the housing are opaque to both types of radiation. The holder 1 containing the substance 6 may be covered with a reversible opaque flap 30, so that radiation passing through the holder and the substrate cannot emerge. The inner side of the flap is preferably provided with an absorbing coating 31.

If the photodiode 21 receives radiation, it supplies a signal Se which, possibly after further processing, for example amplification in an electronic control circuit 30, can be used for causing a LED 31 arranged in the surface 28 of the housing 25 to light up. Instead of a LED or another light-emitting element, the signal Se may also activate a buzzer or bell (32, FIG. 4) so that the presence of the given virus in the substance is indicated by a sound signal. Other, known signaling methods may of course be used alternatively.

Instead of a photodiode, another detector such as a photosensitive tube, for example a photomultiplier tube, may be used. The diode laser and the photodiode have the advantage that they are small and inexpensive so that the novel device can be implemented in a compact and inexpensive way.

In the device of FIG. 2, use is made of the frequency-doubling, or wavelength-halving effect, of the dipolar layer formed upon a reaction of a virus with an antibody. If the holder is irradiated at two different wavelengths, for example from two diode lasers irradiating the same part of the substrate, use may be made of the frequency-summing or frequency-subtracting effect of the dipolar, non-linear optical layer. The filter 20 should then be implemented in such a way that it only passes radiation at the sum frequency or the difference frequency.

Figure 3:
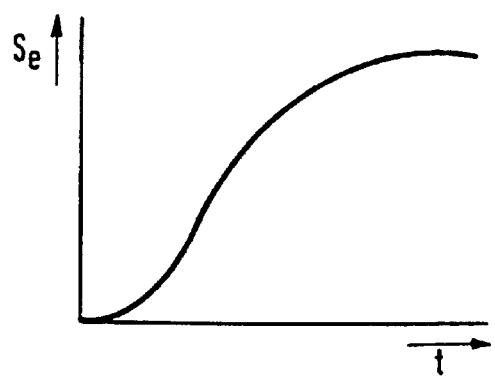
FIG. 3 shows the variation of the detector signal in such a device as a function of time.

Instead of detecting whether a dipolar layer has formed after an incubation period has finished, the rate of formation of such a layer may also be detected. Assuming that a specific rate of formation is associated with each combination of a virus and an antibody, the identity of the virus or the antibody can be determined. FIG. 3 shows, by way of example, the variation of the detector signal Se as a function of time t in arbitrary units for a combination of a given virus and a given antibody which react with each other. The time dependence of this signal can be determined in the electronic circuit 30 and in known manner. This value can be compared with a reference value table stored in a memory of the electronic circuit, from which values the identity of the virus or the antibody can be established.

Figure 4:
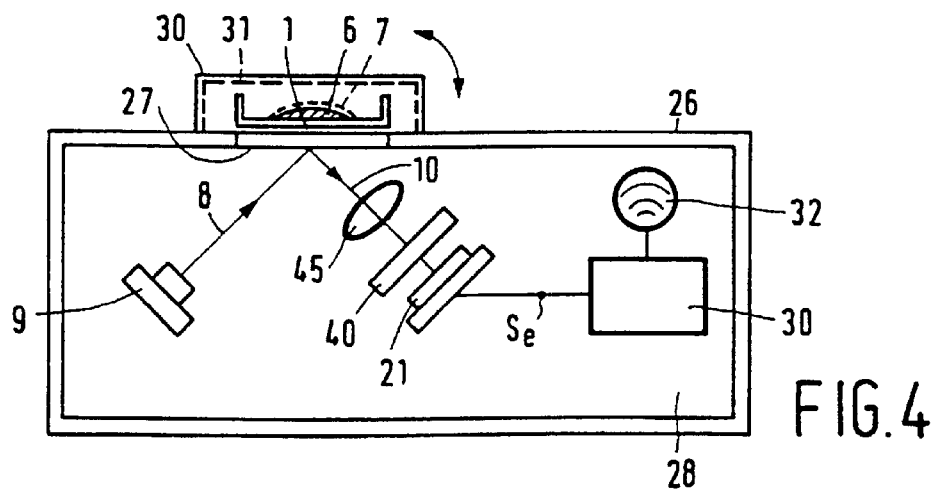
FIG. 4 shows a second embodiment of the device.

FIG. 4 shows a second embodiment of the device which differs from that of FIG. 2 in that the optical filter is replaced by a luminescent plate 40. This plate contains molecules which are brought to a higher state of energy by the radiation 10 and, upon decay to a lower state of energy, emit radiation at a different wavelength. Such a plate can be used if a photodiode, or another detector, is to be used which is less sensitive or insensitive to radiation reflected by the substrate and whose frequency is changed by a non-linear optical layer.

As is shown in FIG. 4, the device may accommodate a lens system 45 for concentrating a maximal quantity of the reflected radiation on the photodiode, if the substance surface to be examined reflects diffusely. This lens system may of course also be arranged in the device shown in FIG. 2.

Since the color difference between, for example, the red radiation incident on the substance 6 and, for example, the blue radiation reflected when a virus has reacted with an antibody, is so large, this difference may also be directly observed by the human eye, so that the detection system shown in FIGS. 2 and 4 does not need to be used, if use is made of the frequency-doubling effect of a non-linear optical layer. It should then be ensured that the observer cannot look directly into the laser radiation.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A device for ascertaining one of: a presence and absence of a binding of a first reactant and a second reactant, wherein upon binding, the first and second reactants form a dipolar layer which displays a non-linear optical behavior at an interface formed between the mutually bound first and second reactants, the device comprising:

a rectangular housing, a transparent sample holder disposed on a wall of said rectangular housing to accommodate the first and the second reactant, a radiation source for supplying a radiation beam having at least one discrete frequency, to irradiate the transparent sample holder, a detection system for detecting radiation returned from the transparent sample holder having a frequency which differs essentially from said at least one discrete frequency indicating the presence of said dipolar layer, which presence is a result of said binding, wherein the wall of the rectangular housing, within which said radiation source and detection system reside, includes a transparent section which faces the radiation source and detecting system whereupon said transparent sample holder is disposed to be irradiated by said radiation beam.

2. A device as claimed in claim 1 wherein a lens system is arranged between the support and a radiation-sensitive element of the detection system.

3. A device as claimed in claim 1 wherein the detection system comprises successively a filter which passes only radiation into an electric signal.

4. A device as claimed in claim 1 wherein the detection system comprises a radiation-sensitive element which converts radiation into an electric signal, proceeded by a luminescent element which converts the radiation having the changed frequency and coming from the holder into radiation having a frequency to which said radiation-sensitive element is sensitive.

5. A device as claimed in claim 1 wherein the radiation source comprises a diode laser.

6. A device as claimed in claim 1 wherein the radiation-sensitive element comprises a photodiode.

* * * * *